US006974962B2

(12) United States Patent
Brill et al.

(10) Patent No.: US 6,974,962 B2
(45) Date of Patent: Dec. 13, 2005

(54) LATERAL SHIFT MEASUREMENT USING AN OPTICAL TECHNIQUE

(75) Inventors: Boaz Brill, Rehovoth (IL); Moshe Finarov, Rehovoth (IL); David Scheiner, Ganel Yehuda (IL)

(73) Assignee: Nova Measuring Instruments Ltd., Rehovot (IL)

(*) Notice: Subject to any disclaimer, the term of this patent is extended or adjusted under 35 U.S.C. 154(b) by 21 days.

(21) Appl. No.: 10/257,544

(22) PCT Filed: Sep. 20, 2001

(86) PCT No.: PCT/IL01/00884

§ 371 (c)(1),
(2), (4) Date: Feb. 6, 2003

(87) PCT Pub. No.: WO02/25723

PCT Pub. Date: Mar. 28, 2002

(65) Prior Publication Data

US 2003/0190793 A1    Oct. 9, 2003

(30) Foreign Application Priority Data

Sep. 19, 2000 (IL) ............................. 138552

(51) Int. Cl.[7] ............................................. G01N 21/86
(52) U.S. Cl. ..................... 250/548; 356/400; 356/401
(58) Field of Search ............................ 250/559.3, 548; 356/400, 401; 430/5, 22, 30; 355/53, 77

(56) References Cited

U.S. PATENT DOCUMENTS

| 5,216,257 | A | * | 6/1993 | Brueck et al. ............... 250/548 |
| 5,808,742 | A | * | 9/1998 | Everett et al. ............... 356/509 |
| 5,877,861 | A | * | 3/1999 | Ausschnitt et al. ......... 356/401 |
| 6,023,338 | A | * | 2/2000 | Bareket ....................... 356/401 |
| 6,079,256 | A | * | 6/2000 | Bareket ....................... 73/105 |
| 6,157,452 | A | * | 12/2000 | Hasegawa et al. .......... 356/401 |
| 6,417,922 | B1 | * | 7/2002 | Dirksen et al. ............. 356/401 |
| 6,462,818 | B1 | * | 10/2002 | Bareket ....................... 356/401 |
| 6,484,060 | B1 | * | 11/2002 | Baluswamy et al. .......... 700/58 |
| 6,486,954 | B1 | * | 11/2002 | Mieher et al. .............. 356/401 |
| 6,606,152 | B2 | * | 8/2003 | Littau et al. ................ 356/124 |
| 6,633,831 | B2 | * | 10/2003 | Nikoonahad et al. ....... 702/155 |
| 6,699,624 | B2 | * | 3/2004 | Niu et al. ....................... 430/5 |
| 6,710,876 | B1 | * | 3/2004 | Nikoonahad et al. ....... 356/401 |

FOREIGN PATENT DOCUMENTS

| EP | 0 281 030 A2 | 9/1988 |
| EP | 0 445 871 A1 | 9/1991 |
| EP | 0 634 702 A1 | 1/1995 |
| EP | 0 816 926 A2 | 1/1998 |
| EP | 0 818 814 A2 | 1/1998 |

OTHER PUBLICATIONS

Niu et al., "Specular Spectroscopic Scatterometry", May 2001, IEEE Transactions on Semiconductor Manufacturing, vol. 14, No. 2, pp. 97-111.*
http://wwww.ieee.org/organizations/pubs/newsletters/leos/oct00/scatter.htm.*

(Continued)

Primary Examiner—Stephone B. Allen
Assistant Examiner—Davienne Monbleau
(74) Attorney, Agent, or Firm—Browdy and Neimark, PLLC

(57) ABSTRACT

The method for controlling layers alignment in a multi-layer sample (10), such a semiconductors wafer based on detecting a diffraction efficiency of radiation diffracted from the patterned structures (12, 14) located one above the other in two different layers of the sample.

17 Claims, 6 Drawing Sheets

OTHER PUBLICATIONS

H.E. Korth; "Phase-Sensitive Overlay Analysis Spectrometry"; *IBM Technical Disclosure Bulletin*; Mar. 1990; pp. 1-3.

R. Krukar et al; Overlay and Grating Line Shape Metrology Using Optical Scatterometry: Final Report; Aug. 31, 1993, DARPA.

* cited by examiner

LATERAL SHIFT MEASUREMENT USING AN OPTICAL TECHNIQUE

FIELD OF THE INVENTION

This invention is generally in the field of manufacturing of multi-layer structures, such as semiconductor wafers and integrated circuits, and relates to an optical measuring method and system for control of layers alignment.

BACKGROUND OF THE INVENTION

Integrated circuits are multi-layer structures produced by applying a sequence of deposition-lithography-etching steps to a semiconductor wafer. In such structures layers have to be precisely aligned with each other, which is controlled by the so-called "overlay measurement". This measurement is usually accomplished using a box-within-a-box technique consisting of the following. A rectangular frame-like structure is formed in a test site of each layer, and two adjacent layers are considered as being correctly aligned if a specific alignment between the frames on these layers is provided. Overlay defining the alignment is measured by comparing the shifts between the frames at opposite sides: determining whether the frames are precisely concentric, the smaller frame being inside the larger one (in projection).

The above technique is carried out by an ordinary optical microscope, which is capable of measuring line width with a resolution limited by resolution of optical imaging systems, usually not less than several nanometers. The current high-performance semiconductor devices, however, have features' dimensions of 0.13 $\mu$m and less, and require measurements of overlay registration with the resolution of less than 1 nm.

A different alignment technique is disclosed in the U.S. Pat. No. 5,216,257. According to this technique, two grating structures of different periodicity are deposited on two adjacent layers in a multi-layer structure, and a change in a moire fringe pattern caused by the superposition of two gratings is detected, being indicative of a grating alignment error.

SUMMARY OF THE INVENTION

There is a need in the art to facilitate overlay measurements for the purpose of correct alignment of layers in a multi-layer sample (e.g., integrated circuit), by providing a novel optical method and system.

The main idea of the present invention is based on the fact that the diffraction of incident radiation from a pair gratings (or any other diffractive structures), located one on top of the other is affected by all geometrical aspects of the gratings, namely, both the parameters of each separate grating and their location relative to each other (i.e., lateral shift). According to the present invention, the lateral shift between two layers is determined by analyzing electromagnetic radiation light) diffracted from gratings (patterned structure) of substantially the same periodicity, which are specifically arranged within a site formed by regions of two layers. To this end, scatterometry (measuring diffraction efficiency as a function of wavelength and/or angle of incidence) or ellipsometry (measuring both change of polarization amplitude and phase of the diffracted light) can be utilized. These techniques are based on the detection of the so-called "diffraction signature" of two gratings one on top of the other.

Thus, according to the invention, an effect of radiation diffraction from two patterned structures (gratings) of known periodicity located one on top of the other, caused by a lateral shift between the two patterned structures, is detected and analyzed to determine an alignment error. The patterned structures are located within a site formed by two regions of two layers, respectively. Preferably, two patterned structures (gratings) of substantially the same periodicity are used.

According to different embodiments of the invention, the following methods are used: a so-called "direct method", a method based on reference sites, and a method based on simple calibration. The direct method is based on the initial calculations of a diffraction signature using certain well-defined models. The reference sites method is based on the comparison between diffraction signatures measured in different sub-regions of the site. The simple calibration based method utilizes certain reference data previously obtained by any suitable tool to be indicative of various diffraction signatures corresponding to respective lateral shifts. These different methods require different sites prepared on the layers of a multi-layer sample.

The term "site" used herein signifies a location in a multi-layer sample that includes two regions one on top of the other. Such a site may be a test site located outside the features containing area if a sample.

If layers' shift along more than one axis in the sample plane is to be determined, the test site (generally, grating containing site) includes two main regions, one containing a grating structure aligned along the X-axis of the sample and the other along the Y-axis of the sample. Each region may contain several different sub-regions having different nominal shifts between the gratings. The term "nominal" signifies a shift of the masks used for layer manufacturing, assuming perfect masks production and zero alignment error.

Another embodiment of the test structure may contain a two-dimensional grating enabling the measurement of the X and the Y components of the lateral shift at the same site. In order to avoid the possibility to confuse between the X and the Y components several methods may be used: (a) Produce a test site whose period in the Y-axis is significantly different than the period in the X-axis (b) measure the same site several times using different polarizations (in case of polarized reflectometry) (c) measure the same site from different directions. All the above methods result in different changes to the diffraction signatures due to shifts in different directions, thus avoiding confusion.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
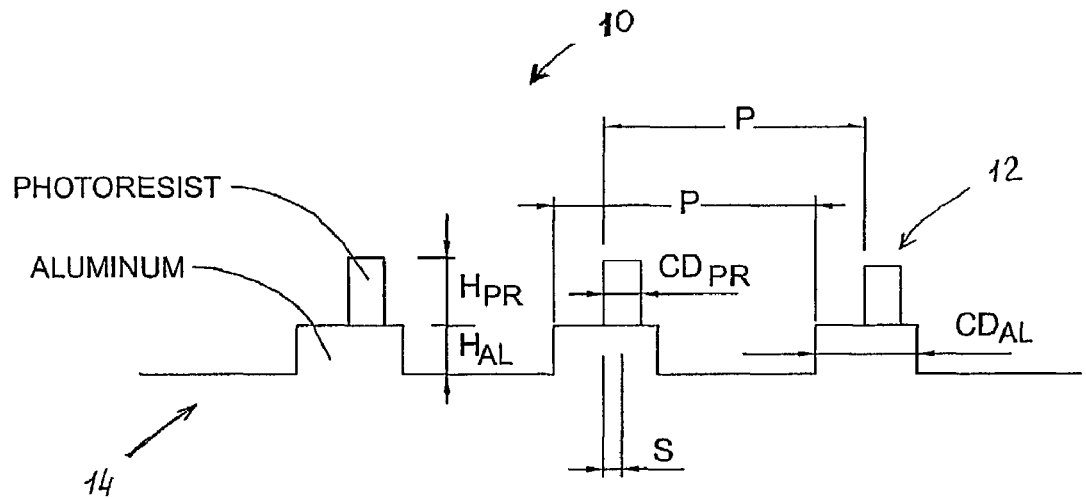
FIG. 1 is a schematic illustration of a cross-section of a site in a semiconductor wafer.

Referring to FIG. 1, there is schematically illustrated a cross-section of a test site 10 in a semiconductor wafer suitable for use in the present invention. The site 10 contains two gratings (patterned structures) 12 and 14 of certain known periodicity located one above the other. In the present example, the gratings 12 and 14 have substantially the same period P. In the present example, the top grating 12 presents a pattern of spaced-apart photoresist-containing regions $R_{PR}$, and the underneath grating 14 presents a pattern of spaced-apart aluminum-containing region $R_{Al}$. In this specific example, the gratings 12 and 14 have different duty cycles defined by features critical dimensions $CD_{PR}$ and $DC_{Al}$, respectively. It should, however, be noted that this condition is not a requirement for the technique of the present invention, but provides for a better sensitivity of the method. As further shown in the figure, the gratings 12 and 14 are shifted along the X-axis with respect to each other a distance S, which is measured as a distance between the centers of the two locally adjacent regions (lines) $R_{PR}$ and $R_{Al}$.

In order to find the conditions under which the method of the present invention is most effective, and show how the method is practical, the sensitivity of the method has been studied for a specific configuration of the site structure exemplified in FIG. 1. The site structure 10 is typical for the overlay problem in photoresist-on-aluminum layer structure. The pattern in the aluminum (Al) layer is typically defined by layers underneath the aluminum layer, and the photoresist (PR) layer is patterned by a lithography processing. In this specific example, the PR lines are modeled to be on top of the Al lines. It should, however, be understood, that this is not essential for the present invention, and PR lines may be located between the Al lines, as well. For simplicity, both gratings 12 and 14 have a square profile. The measurement technique used for this analysis is the normal incidence polarized spectrophotometry. According to this technique, the normal incidence reflectivity spectrum is measured with selective polarization direction of the incident light relative to the grating (TM polarization mode in this specific example). Other optical techniques, such as spectral ellipsometry, angular scatterometry, etc. may be used as well.

The sensitivity of the spectrum (measured by the technique of the present invention, which will be described more specifically further below) to a change in the lateral shift S between the gratings 12 and 14 has been studied. The ratio between the mean change in the spectrum (defined as the root of the mean of the square differences between spectra with and without a change in the shift) caused by a change in the shift value S of 1 nm has been defined as the sensitivity test T, wherein S is the nominal shift.

The simulation results have shown that T depends on all the parameters of the test structure. Values of T are almost always monotonously increasing with the values of S. This general rule holds as much as T can be increased, i.e., until the edge of the PR line "falling off" from the Al line. It is thus evident that the measurement is more sensitive for an asymmetrical structure.

As for the other parameters of the test site, such as the period P, the $CD_{PR}$ and $CD_{Al}$ (generally, the duty cycles of gratings) and the heights $H_{PH}$ and $H_{Al}$ of the two gratings, they usually affect the sensitivity test T in an oscillatory manner. It is thus necessary to find such a set of gratings parameters, that T is maximized while being least sensitive to the exact values of these parameters. For example, the value of T equal to $8 \cdot 10^{-3}$ is obtained with the following set of gratings' parameters: P=600 nm, $CD_{PR}$=300 nm, $CD_{AL}$=150 nm, $H_{PR}$=600 nm, and $H_{AL}$=100 nm.

In one embodiment of the invention, the direct method is used. In this method exact simulation methods, such as RCWT (Rigorous Couple Wave Theory), are used to simulate the diffraction signature(s) from the test site. In the simplest case there is not any prior knowledge of the exact grating properties on either layers. In this case the experimentally measured diffraction from the test site is fitted to simulation fitting at the same time for both CD's, grating heights and additional parameters characterizing the individual gratings in the two layers and the shift as an additional fitting parameter.

Figure 2A:
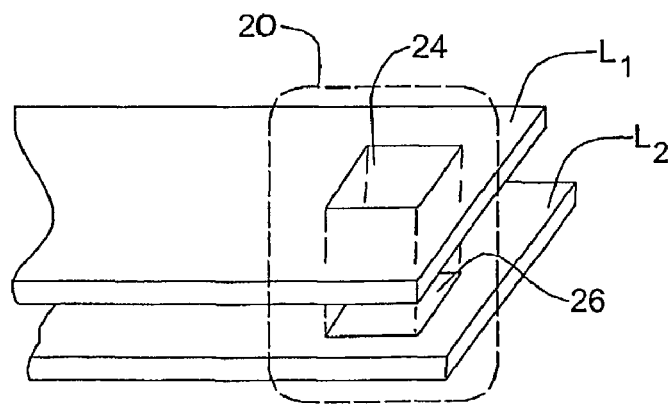
FIGS. 2A and 2B illustrate the principles of a direct method according to the invention.
Figure 2B:
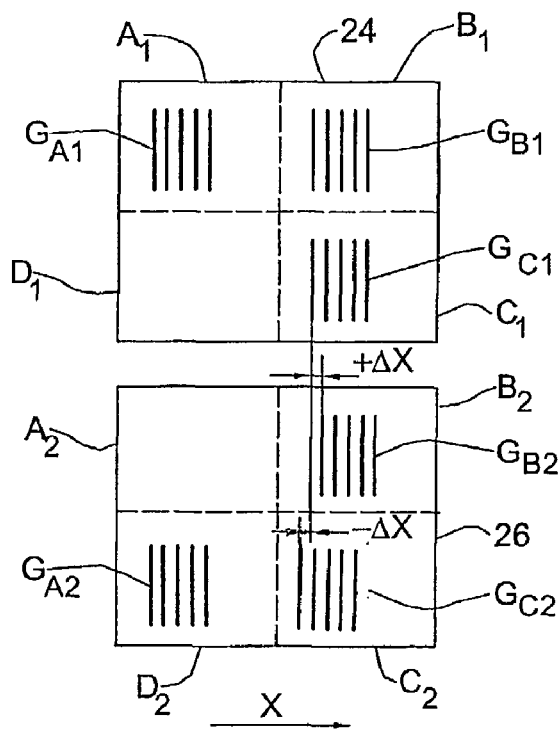

FIGS. 2 and 2B exemplify the principles underlying the design of a test site 20 suitable to be used for another embodiment of the present invention. The test site 20 is formed by regions 24 and 26 located one on top of the other in layers $L_1$ and $L_2$, respectively. As shown in FIG. 2B, the two regions 24 and 26 define together four different pairs of sub-regions: $A_1$–$A_2$, $B_1$–$B_2$, $C_1$–$C_2$ and $D_1$–$D_2$, wherein sub-regions $A_2$, $B_2$, $C_2$ and $D_2$ are located on top of sub-regions $A_1$, $B_1$, $C_1$ and $D_1$, respectively. In the pair $A_1$–$A_2$, sub-regions $A_1$ and $A_2$ are different in that region $A_1$ contains a grating $G_{A1}$ and sub-region $A_2$ has no grating at all, and in the pair $D_1$–$D_2$—vice versa. Gratings $G_{B1}$ and $G_{B2}$ of sub-regions $B_1$ and $B_2$, respectively, are shifted with respect to each other along the X-axis a distance $+\Delta x$ (i.e., in the positive X-direction), and gratings $G_{C1}$ and $G_{C2}$ are shifted with respect to each other a distance $-\Delta x$ (negative X-direction). In this embodiment information is gained from measuring the single-grating sites (sub regions $A_1$–$A_2$ and $D_1$–$D_2$) in order to simplify the fitting in the dual-grating sites (sub regions $B_1$–$B_2$ and $C_1$–$C_2$). The measurement is done in two steps. In the first step the single-grating sites are measured and the grating characteristics in those sites, including for example CD, height wall angle etc., are measured by fitting to simulation, as in normal scatterometry. In the second step the measurements of the dual-grating sites are fitted to simulation using all or part of the grating parameters that have been measured in Step 1 and fitting for the shift between the gratings. It should be noted that at least those gratings which are located in a common layer must be are identical, i.e., have the same period, duty cycle, and height.

Notice that for the case of perfect alignment the measurements of sites B and C should be identical, thus a significant difference between the two measurement may indicate an alignment error. The difference between the two signals obtained from sub-region pairs $B_1$–$B_2$ and $C_1$–$C_2$, respectively, may be utilized in order to increase the sensitivity and reduce systematic measurement errors. This can be done by fitting the difference of simulated signatures to the difference of the measurements in the two sites. This procedure may be used in order to filter out changes in the spectrum that are not related to the shift S, thus enhancing the sensitivity and the robustness of the measuring technique.

Figure 3:
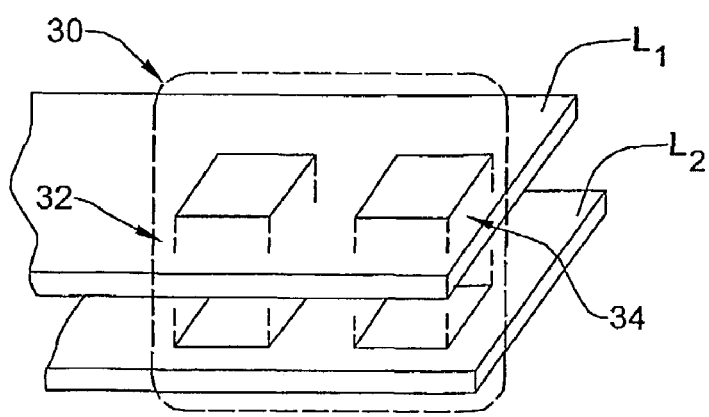
FIG. 3 illustrates the principles of a reference sites based method according to the present invention.

In another embodiment of the invention, the reference site method is used. FIG. 3 illustrates the main principles underlying this method. Here, a test site 30, which is formed by two regions one above the other in layers $L_1$ and $L_2$, is composed of a so-called "measurement site" 32 and a so-called "reference site" 34 spaced-apart from each other along the X-axis. Gratings in these sites are not specifically illustrated, but is should be understood that both the measurement and the reference sites include sub-region pairs arranged as described above. In this method, the measurement site 32 has one grating-pair characterized by a nominal shift (+ΔX) between the gratings, and the reference site 34 has several grating-pairs located in sub-region pairs, respectively, aligned in a spaced-apart relationship along the X-axis and characterized by the following nominal shifts: −ΔX−3Δx, −ΔX−2Δx, −ΔX−Δx, −ΔX, −ΔX+Δx, −ΔX+2Δx, −ΔX+3Δx, . . . etc., Δx is typically much smaller than ΔX and is of the same order of magnitude as the required resolution in the lateral shift measurement. In this method, it is assumed that the grating profiles are sufficiently symmetric and unaffected by the exact shift, and therefore symmetric shifts between the gratings (upper grating shifted to either right or left of the lower grating) will result in the identical diffraction signatures.

When the two layers are printed with an alignment error (+ξ), the actual shifts between the gratings of the measurement site will be: (+ΔX+ξ) and for the reference sites the shifts will be as follows:

(−ΔX−3Δx+ξ); (−ΔX−2Δx+ξ); (−ΔX−Δx+ξ);
(−ΔX+ξ); (−ΔX+Δx+ξ); (−ΔX+2Δx+ξ); etc.

In order to measure the alignment error ξ, the diffraction signatures from all the sub-region pairs are measured using one of the above mentioned measurement techniques. Then, the signature from the measurement site is compared to the signatures from all the sub-region pairs in the reference site, looking for the best match. If the best match is found for the $(+N)^{th}$ sub-region pair, for which the nominal shift is (−ΔX+NΔx), than we have:

(+ΔXr+ξ)≈−(−ΔXr+NΔx+ξ)

and therefore:

ξ≈(−NΔx)/2

Hence, the shift with the resolution of Δx/2 can be found by simply finding the best matching signature from the set.

If a significant range of shifts is to be covered by a small number of sub-region pairs in the reference site, Δx should be selected to be significantly larger than the required resolution. In this case, some interpolation method can be used in order to find the shift with improved accuracy. Interpolation can be done, for example, by calculating the RMS (root mean square) of the difference between the measurement site signature and all reference site signatures, fitting all or part of the results to a polynomial function of the shift and finding the shift providing minimum RMS difference in signatures. Another optional interpolation method is using a learning system, which is trained using the reference site data to return the shift, and measurement site data is used as input for interpretation. Comparing the reference site method to the direct method, the reference site method is advantageously self-calibrating, i.e., there is no need to realize the potentially complex details about how the diffraction signature was created, including materials properties and exact geometry (e.g. CD, line profile), as long as these are constant for all involved sites. The reference site method, however, requires a larger area on the sample occupied by a test site and a larger number of measurements, requiring more time.

In yet another embodiment of the invention, a calibration method may be used. In this method, a test site similar to the test site 20 of FIGS. 2A and 2B (suitable to be used for direct method) but including only two grating-containing sub-region pairs $B_1$–$B_2$ and $C_1$–$C_2$ is used. Here, similarly to the direct method, the difference between the diffraction signatures measured on both sub-region pairs is determined, but, in distinction to the direct method, the resulting signature is not fitted to a theoretical signature, but is rather interpreted using a previously performed calibration stage. In the calibration stage, the signature (or only some sensitive points thereof) is determined as a function of alignment error values, being measured by a suitable reference tool (e.g., ordinary microscope). To this end, a test sample (e.g., semiconductor wafer) is specifically prepared with several alignment shifts, and measured off-line to make a record of the calibration results and keep it as reference data.

In accordance with still another embodiment of the test structure may contain a two-dimensional grating enabling the measurement of the X and the Y components of the lateral shift at the same site. In that case, in order to avoid the possibility to confuse between the X and the Y components further several methods may be used. In accordance with one embodiment, test site is prepared, comprising two dimension grating with a period in the Y-axis significantly different than the period in the X-axis. In accordance with another embodiment polarized reflectometry technique may be used to measure the same site several times with different polarizations. Finally, the same site may be measured from different directions (with different orientation). All the above methods result in different changes to the diffraction signatures due to shifts in different directions, thus avoiding confusion.

Figure 4:
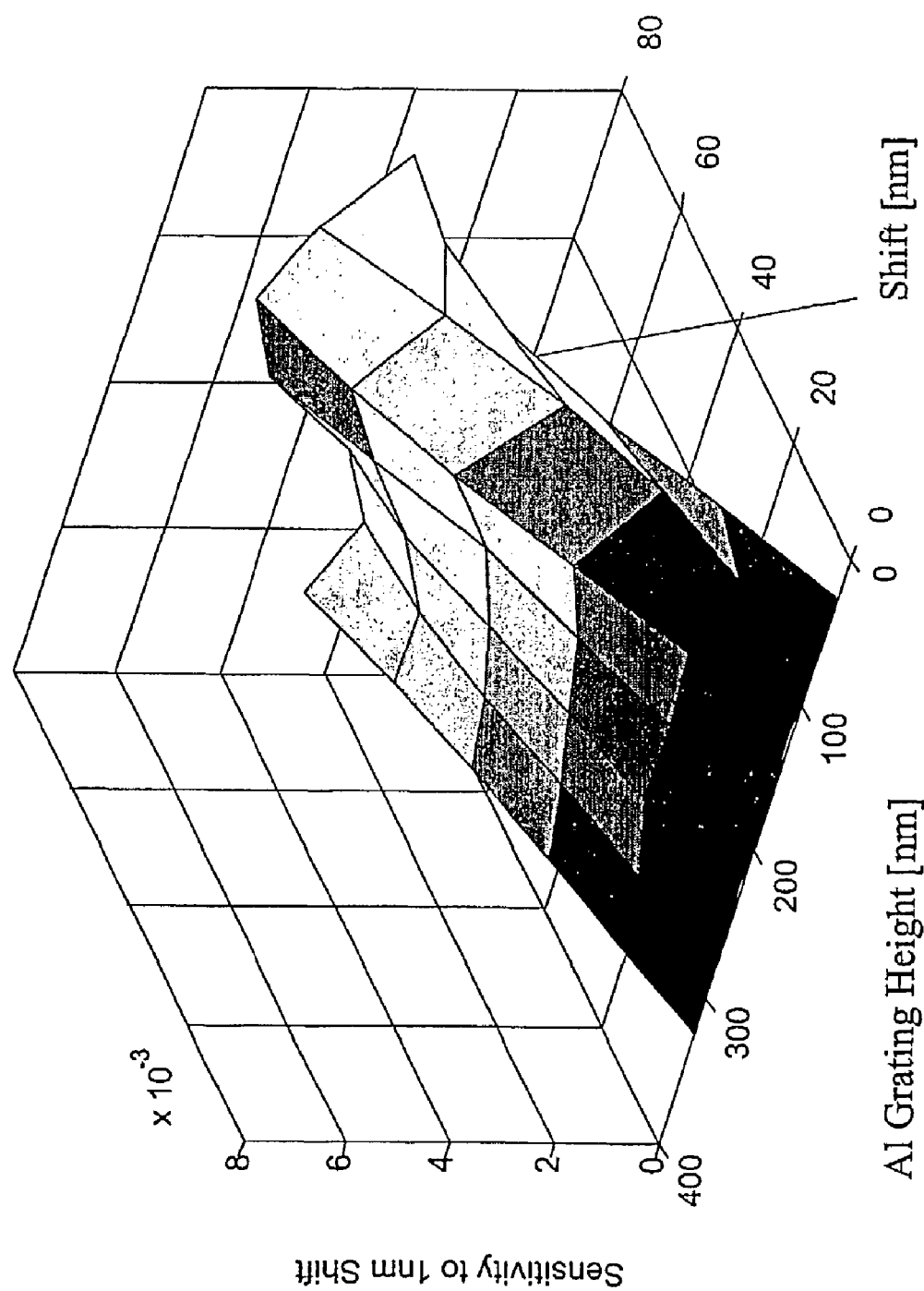
FIGS. 4–6 illustrate different simulation results of the sensitivity test as functions of grating parameters.
Figure 5:
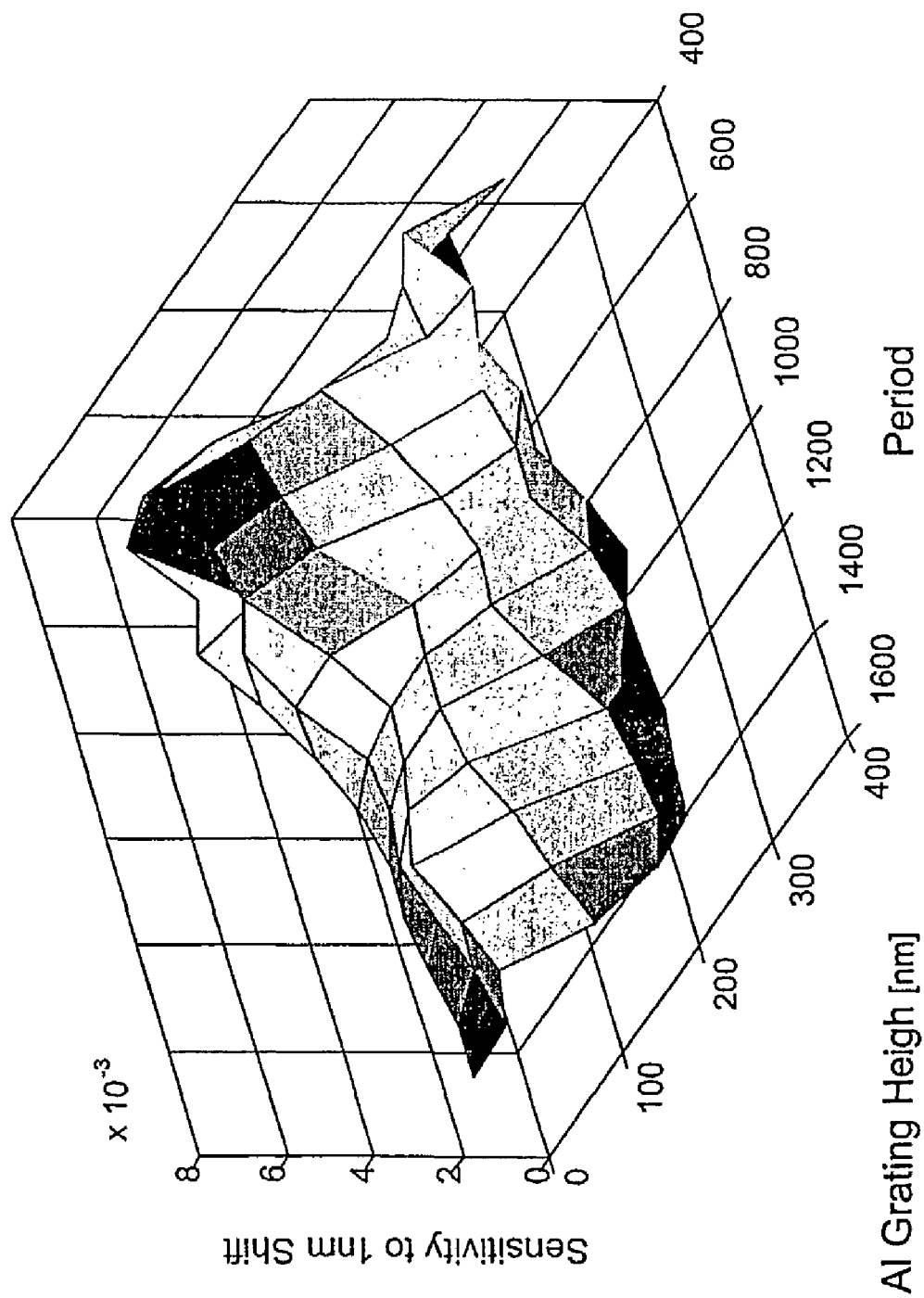
Figure 6:
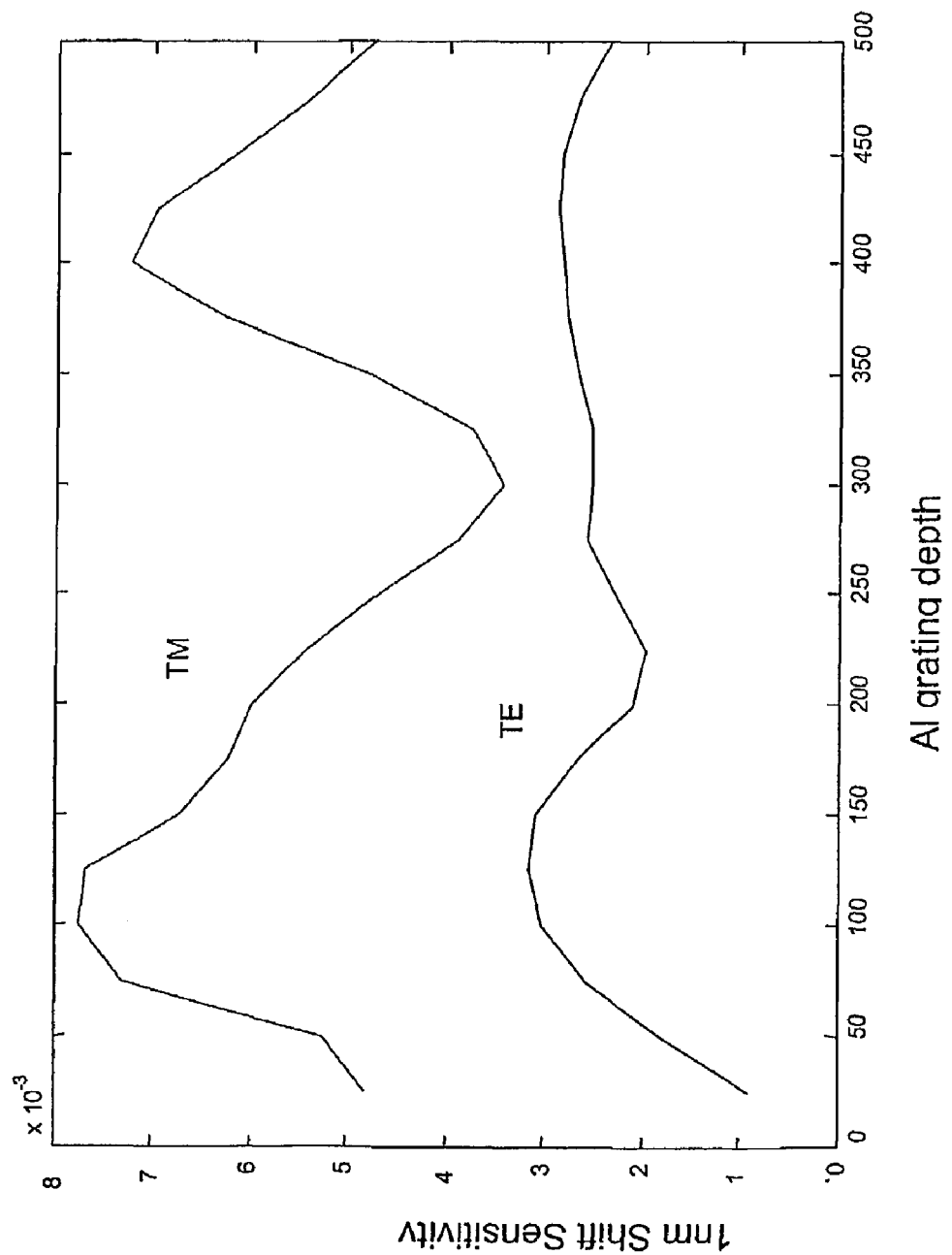

Reference is now made to FIGS. 4–6 showing different simulation results of the sensitivity test as functions of grating parameters. FIG. 4 illustrates the sensitivity test as a function of Al grating depth ($H_{Al}$) and shift S using the test structure of FIG. 1 with the following parameters: $CD_{PR}$=150 nm, $CD_{Al}$=300 nm, P=800 nm and $H_{PR}$=600 nm. FIG. 5 illustrates the sensitivity test as a function of Al grating depth ($H_{Al}$) and grating period P using the test structure of the following parameters: $CD_{PR}$=150 nm, $CD_{Al}$=300 nm, $H_{PR}$=600 nm and S=75 nm. FIG. 6 illustrates the sensitivity test as a function of Al grating depth using the test structure of the following parameters: $CD_{PR}$=150 nm, $CD_{Al}$=300 nm, P=600 nm and $H_{PR}$=600 nm. Two graphs R1 and R2 are shown corresponding, respectively, to TM and TE polarization modes of incident radiation relative to the grating orientation.

Figure 7:
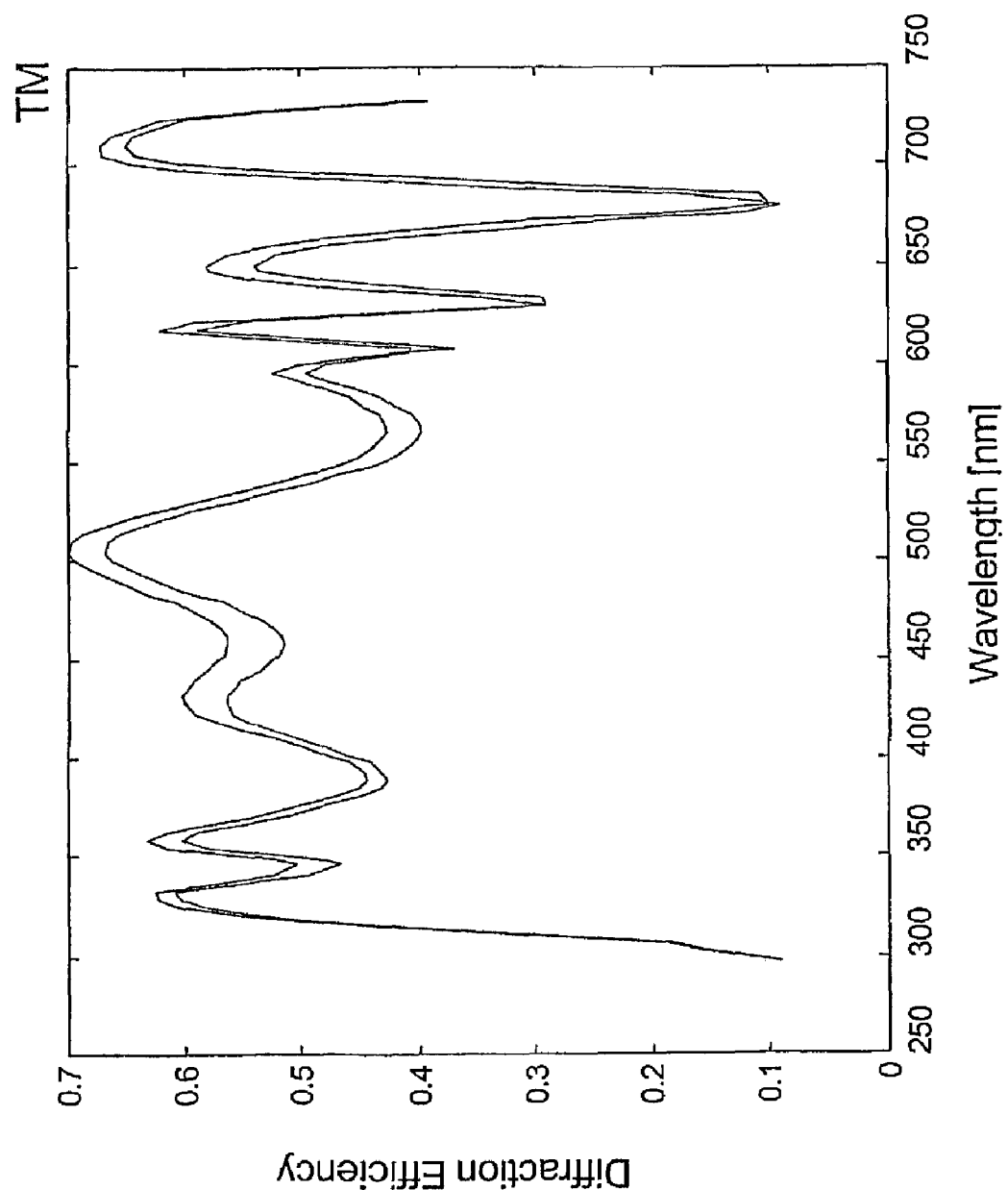
FIG. 7 illustrates the effect of an overlay error on a scatterometry signal (diffraction efficiency) as measured on the optimal structure.

FIG. 7 illustrates the effect of a 5 nm overlay error on a scatterometry signal (diffraction efficiency) measured on the optimal structure with the TM polarization mode. Two diffraction signatures $SG_1$ and $SG_2$ are shown corresponding, respectively, to a sample with no lateral shift between the layers (i.e., overlay is zero) and to a sample with a 5 nm overlay error.

Obviously, many modifications and variations of the present invention are possible in the light of the above teachings. For example, in the reference site based method grating-pairs located in sub-region pairs may be characterized by pre-determined arbitrary nominal shifts.

Those skilled in the art will readily appreciate that many modifications and changes may be applied to the invention as hereinbefore exemplified without departing from its scope, as defined in and by the appended claims.

What is claimed is:

1. A method for controlling layers alignment in a multi-layer sample, the method comprising:
   (i) providing a measurement site including two patterned structures located one above the other in two different layers, respectively;
   (ii) illuminating said site with electromagnetic radiation thereby illuminating one of the patterned structures through the other, and detecting a diffraction efficiency of radiation diffracted from the patterned structures indicative of a lateral shift between the patterned structures; and (iii) analyzing said diffraction efficiency to determine an existing lateral shift between the layers.

2. The method of claim 1, wherein said pattern structures characterized by substantially the same periodicity.

3. The method of claim 2, further comprising the step of providing at least one additional site including two regions located one above the other in two different layers, respectively, said regions in said additional site containing patterned structures; illuminating said additional site with electromagnetic radiation and detecting diffraction efficiency of radiation diffracted from the patterned structures and analyzing the diffraction efficiencies obtained in said additional site to determine an existing lateral shift between the layers.

4. The method of claim 3, wherein the pattern structures located in two different layers of the measurement site are shifted with respect to each other along the X-axis by a distance $+\Delta X$ and the pattern structures located in two different layers of the additional site are shifted with respect to each other along the X-axis by a distance $-\Delta X$.

5. The method of claim 4 further comprising the step of providing additional sites including regions containing pattern structures in one of the layers.

6. The method of claim 3 wherein the pattern structures located in two different layers of the measurement site are shifted with respect to each other along the X-axis by a distance $+\Delta X$ and the pattern structures located in two different layers of the additional sites are shifted with respect to each other along the X-axis by a distance $-\Delta X \pm N\Delta x$, wherein $\Delta x << \Delta X$ and N is an integer number.

7. The method of claim 3, wherein at least one of additional sites comprising pattern structures at essentially right angle to the pattern structures of the measurement site.

8. The method of claim 1 wherein said detecting a diffraction efficiency of radiation diffracted from the patterned structures indicative of a lateral shift between the patterned structures comprising measuring said diffraction efficiency as a function of wavelength.

9. The method of claim 1 wherein said detecting a diffraction efficiency of radiation diffracted from the patterned structures indicative of a lateral shift between the patterned structures comprising measuring said diffraction efficiency as a function of angle of incidence.

10. The method of claim 1 wherein said detecting a diffraction efficiency of radiation diffracted from the patterned structures indicative of a lateral shift between the patterned structures comprising measuring said diffraction efficiency as a function of angle of reflection.

11. The method of claim 1 wherein said detecting a diffraction efficiency of radiation diffracted from the patterned structures indicative of a lateral shift between the patterned structures comprising measuring said diffraction efficiency as a function of angle of incidence and angle of reflection.

12. The method of claim 1 wherein said detecting a diffraction efficiency of radiation diffracted from the patterned structures indicative of a lateral shift between the patterned structures comprising measuring said diffraction efficiency as a function of change of polarization amplitude and phase of the diffracted light 13. The method of claim 1 wherein the step of illuminating said site with electromagnetic radiation comprising illuminating with polarized light with different states of polarization.

14. The method of claim 1 wherein said patterned structures are two-dimensional.

15. The method of claim 14 wherein the periodicity of said two-dimensional patterned structures is different along the X-axis and Y-axis.

16. The method of claim 14 wherein the step of illuminating said site with electromagnetic radiation comprises illuminating with polarized light with different states of polarization.

17. The method of claim 1 wherein said multi-layer sample is a semiconductor wafer.

* * * * *